United States Patent [19]

Carrier

[11] Patent Number: Plant 5,720

[45] Date of Patent: Apr. 15, 1986

[54] CARNATION PLANT

[76] Inventor: Leonard E. Carrier, 1911 Sheridan Rd., Encinitas, Calif. 92924

[21] Appl. No.: 666,922

[22] Filed: Oct. 31, 1984

[51] Int. Cl.[4] ..... A01H 5/00
[52] U.S. Cl. ..... Plt./71
[58] Field of Search ..... Plt./71

*Primary Examiner*—Robert E. Bagwill

*Attorney, Agent, or Firm*—James R. Cypher

[57] ABSTRACT

The present invention relates to a new and distinct cultivar of carnation plant, named Sonja Pink, originated by me by crossing unnamed and unpatented seedlings; distinguished from its parents as well as any other variety known to me by its pink color, its superior resistance to soil borne diseases, and its flowers that open fully without bursting the calyx and causing splits.

1 Drawing Figure

BACKGROUND OF THE INVENTION

The present invention relates to a new and distinct cultivar of carnation plant, named Sonja Pink, which was originated by me by crossing numbered but unnamed and upatented seedlings.

The new cultivar was the result of a breeding program undertaken by me in my commercial nursery at Encinitas, Calif. by cross-breeding numbered but unnamed and unpatented seedlings; nursery numbers 2293 (male) and 2280 (female).

Typically, carnation plants, botanically known as the species *Dianthus caryophyllus,* are very prone to fungi and root rots, and have a tendency to burst their calyx causing "splits" as the flowers open fully. The primary objectives of this breeding program were to produce a cultivar of "new" color combined with greatly improved resistance to soil-borne diseases and "splitting". These objectives were fully achieved, along with other desirable improvements, as evidenced by the following unique combination of principal characteristics which are outstanding in my new cultivar, Sonja Pink, and which distinguish it from its parents, as well as from all other carnations of which I am aware:

1. Superior resistance to soil-borne diseases such as *Fusarium oxysporium,* and *F. roseum* and root-rots such as damping off, water molds, and the like;
2. Medium size spray type flowers which open fully without bursting the calyx and causing "splits";
3. A distinctive and attractive pink flowr color which retains its color without fading.
4. A very vigorous and free-breaking plant habit with strong, straight sprays.

The closest commercial variety to which it compares in color that I am aware of is the Meilland rose, "Sonja".

Asexual reproduction of my new carnation variety by side shoot cuttings rooted in peat and "Perlite" under mist, as performed under my direction and control at Encinitas, Calif. shows that the foregoing characteristics and distinctions come true and are established and transmitted through succeeding propagations.

BRIEF DESCRIPTION OF THE DRAWING

The accompanying color photograph shows typical specimens of the new cultivar in different stages of development (tight buds, partially opened bud and full bloom) and illustrates the vigorous, free-breaking growth habit and strong, straight stems.

DETAILED DESCRIPTION OF THE DRAWING

The following is a detailed description of my new carnation cultivar, Sonja Pink, with color terminology in accordance with Robert Ridgway's Color Standards and Nomenclature (1912 edition).

The following detailed botanical description is based on observations of plants grown inside my commercial greenhouses at Encinitas, Calif.: the height of plant and flower and foliage size established as an average using standard commercial cultural practices.

The data provided accurately characterizes the cultivar in question. Color designation and other values stated may deviate slightly from the stated values from flowering to flowering, but the deviations will be within the range expected from varying environmental, seasonal, and cultural conditions.

Plant:

*Botanical classification.*—*Dianthus caryophyllus.*

*Breeding.*—Female parent: Nursery Number 2280. Male parent: Nursery Number 2293.

*Form.*—Erect but free-branching spray carnation.

*Growth.*—Vigorous and strong.

*Height.*—Medium tall, approximately 80 cm.

*Classification.*—Greenhouse type, suitable for cut flower production as a spray.

*Propagation.*—Holds its distinguishing characteristics through succeeding propagations by rooted cuttings.

*Locality where grown and observed.*—Encinitas, Calif.

*Disease resistance.*—The new cultivar has shown no evidence of fusariums or other root rots, as determined by extensive tests in high infested soils inoculated with as many strains of fungi as are locally available in the area of Encinitas, Calif.; tests conducted without chemical or steam sterilization of the soil (soils in which the carnation plant "Sim" and others soon die).

*Blooming period.*—Bloom under both long and short photoperiods.

*Temperature tolerance.*—Not hardly to cold. Grows best at temperature about 10° C.; has good resistance to hot weather in summer months of August and September at Encinitas, Calif., without hardening of growth and with only little reduction of flower size and little flower fading; no marked fading of outer flower petals even when bloom is past maturity.

Bud: Lobes of calyx overlap in tight bud and seldom split.

*Length.*—2.5 cm.

*Diameter.*—1.2 cm.

*Color.*—Deep dull yellow green (1) Plate XXXII, 31", Y-GK.

Bloom:

*Size.*—5.5 to 6.5 cm.

*Stem.*—Consists of 6 nodes. Length is about 40 cm. Diameter is about 0.5 cm. at base and about 0.3 cm. at base of calyx. Color is Empire Green Plate XXXII, 32" GY-G or Dark American Green Plate XL1, 33" GY-GK.

*Form.*—Round.

*Petalage.*—From 50–60 petals. Outer petals are approximately 2.0 cm. wide and about 4 cm. long. Center petals are about 1.5 cm wide and about 3.5 cm. long.

*Color.*—The center of flower, outer petals, base of petals, and inside of petals is Geramium Pink, Plate 1,3.0-Rd. Reverse of petals is Plate 1, O-R-t. LaFrance Pink.

*General tonality.*—Medium Pink with a rose pink cast.

*Petals.*—Texture is smooth. Form: Long stemmed spatulate, serration 10 to the centimeter, 0.1 cm. deep. Opening: Normal with minimum split calyx.

*Fragrance.*—No distinctive fragrance.

Foliage:

*Form.*—*Flat-concave.*

*Size.*—0.8 cm. wide and 14.0 cm. long.

*Quantity.*—Two leaves per node, with nodes spaced about 4.0 cm. to 10.0 cm. apart.

*Color.*—The upper and under sides of both young and mature leaves are Dark American Green Plate XL1, 32" GY-GK.

*Texture.*—Smooth.

I claim:

1. A new and distinct cultivar of carnation plant named, Sonja Pink, substantially as herein shown and described, characterized particularly as to novelty by the unique combination of superior resistance to soil-borne diseases; medium, slightly serrated flowers which open fully without bursting the calyx and causing "splits"; a distinctive and attractive pink flower color which retains its color without fading; a very vigorous and free-breaking plant habit; strong and straight sprays; and good heat tolerance.

* * * * *

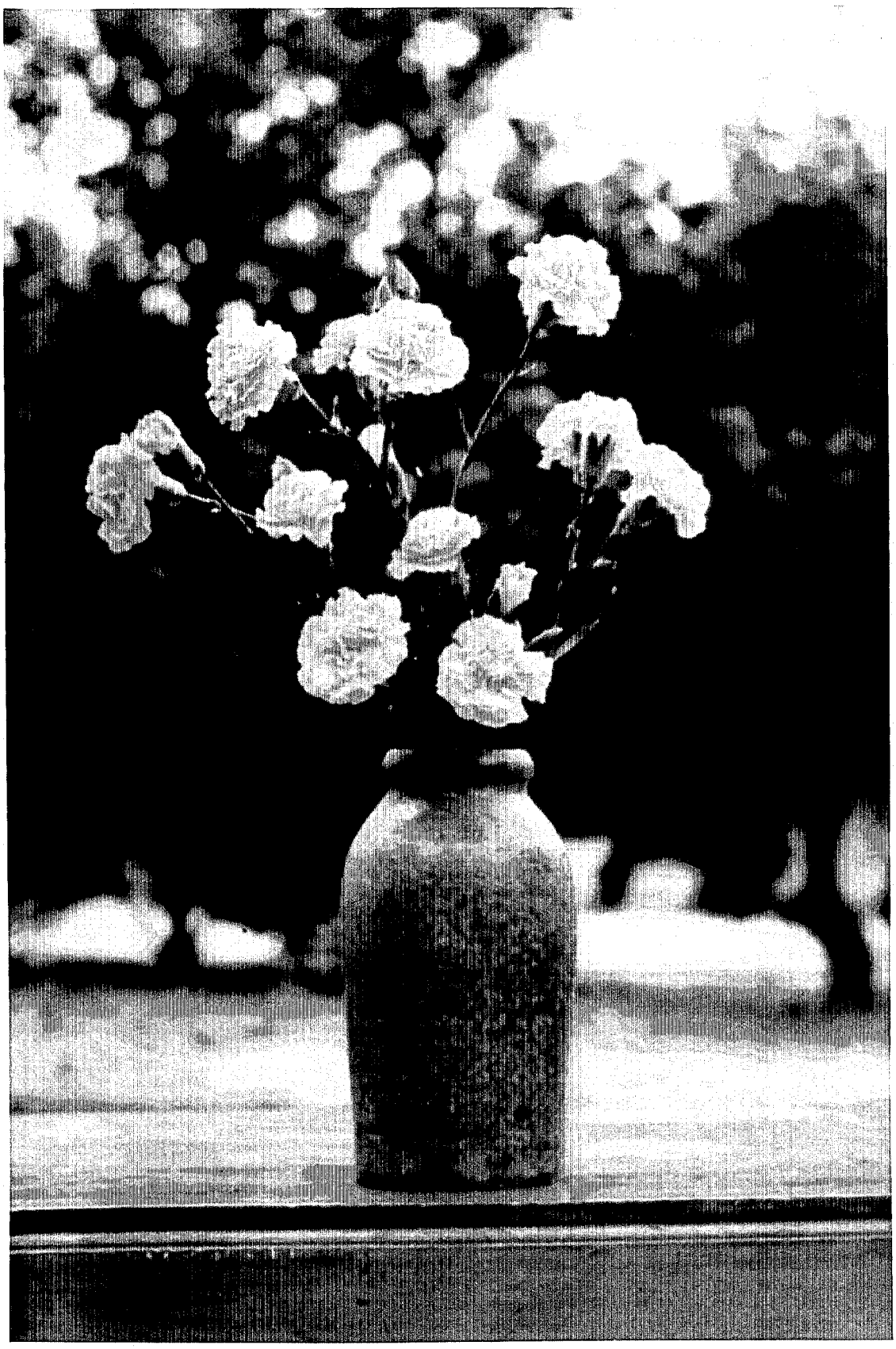

UNITED STATES PATENT AND TRADEMARK OFFICE

CERTIFICATE OF CORRECTION

PATENT NO. : Plant 5720

DATED : April 15, 1986

INVENTOR(S) : Leonard E. Carrier

It is certified that error appears in the above-identified patent and that said Letters Patent is hereby corrected as shown below:

Column 1, line 31, change "flowr" to --- flower---

Column 2, line 46, change "hardly" to ---hardy---

Column 3, line 27, change "Geramium" to --- Geranium---

Signed and Sealed this

*Fifth* Day of *August 1986*

[SEAL]

*Attest:*

DONALD J. QUIGG

*Attesting Officer*

*Commissioner of Patents and Trademarks*